(12) United States Patent
Barbu et al.

(10) Patent No.: US 7,792,342 B2
(45) Date of Patent: Sep. 7, 2010

(54) SYSTEM AND METHOD FOR DETECTING AND TRACKING A GUIDEWIRE IN A FLUOROSCOPIC IMAGE SEQUENCE

(75) Inventors: Adrian Barbu, Plainsboro, NJ (US); Vassilis Athitsos, Newton, MA (US); Bogdan Georgescu, Princeton, NJ (US); Peter Durlak, Erlangen (DE); Stefan Boehm, Oberasbach (DE); Dorin Comaniciu, Princeton Junction, NJ (US)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 830 days.

(21) Appl. No.: 11/675,678

(22) Filed: Feb. 16, 2007

(65) Prior Publication Data

US 2007/0270692 A1 Nov. 22, 2007

Related U.S. Application Data

(60) Provisional application No. 60/774,180, filed on Feb. 16, 2006, provisional application No. 60/868,422, filed on Dec. 4, 2006.

(51) Int. Cl.
*G06K 9/00* (2006.01)
(52) U.S. Cl. .................. 382/128; 382/131; 382/132
(58) Field of Classification Search ............... 382/128, 382/131, 132, 103, 155, 159, 173, 181; 600/374, 600/431, 585, 523
See application file for complete search history.

(56) References Cited

U.S. PATENT DOCUMENTS 6,493,575 B1 * 12/2002 Kesten et al. ............... 600/431

OTHER PUBLICATIONS

Zhuowen Tu; "Probabilistic Boosting-Tree: learning discriminative models for classification, recognition and clustering" Oct. 2005; iccv, vol. 2, pp. 1589-1596, Tenth IEEE International Conference on Computer Vision (ICCV'05) vol. 2, 2005.*

* cited by examiner

*Primary Examiner*—Vu Le
*Assistant Examiner*—Claire Wang (57) ABSTRACT

A system and method for populating a database with a set of image sequences of an object is disclosed. The database is used to detect localization of a guidewire in the object. A set of images of anatomical structures is received in which each image is annotated to show a guidewire, catheter, wire tip and stent. For each given image a Probabilistic Boosting Tree (PBT) is used to detect short line segments of constant length in the image. Two segment curves are constructed from the short line segments. A discriminative joint shape and appearance model is used to classify each two segment curve. A shape of an n-segment curve is constructed by concatenating all the two segment curves. A guidewire curve model is identified that includes a start point, end point and the n-segment curve. The guidewire curve model is stored in the database.

23 Claims, 7 Drawing Sheets

SYSTEM AND METHOD FOR DETECTING AND TRACKING A GUIDEWIRE IN A FLUOROSCOPIC IMAGE SEQUENCE

CROSS REFERENCE TO RELATED APPLICATIONS

This application claims the benefit of U.S. Provisional Application Ser. No. 60/774,180 filed Feb. 16, 2006 and U.S. Provisional Application Ser. No. 60/868,422, filed Dec. 4, 2006, which are incorporated by reference in their entirety.

FIELD OF THE INVENTION

The present invention is directed to a system and method for detecting curves using hierarchical modeling, and more particularly, to a system and method for detecting and tracking a guidewire in a fluoroscopic image sequence.

BACKGROUND OF THE INVENTION

Detection and segmentation of wire-like structures is a challenging problem with many practical applications in both medical imaging and computer vision. An example of such an application is the detection and segmentation of a guidewire from fluoroscopic images used during coronary angioplasty. Coronary angioplasty is a medical procedure used to restore blood flow through clogged coronary arteries. During this minimally invasive procedure, a catheter containing a guidewire is inserted through an artery in the thigh and guided by the cardiologist until it reaches the blocked coronary artery. Then, a catheter with a deflated balloon is inserted along the wire and guided so that the balloon reaches the blockage. At that point, the balloon is inflated and deflated several times so as to unblock the artery. A device called a stent is often placed at that position in order to keep the artery from getting blocked again.

Throughout the procedure, the cardiologist uses fluoroscopic images to monitor the position of the catheter, guidewire, balloon and stent. Fluoroscopic images are x-ay images collected at a rate of several frames per second. In order to reduce the patient's exposure to x-ray radiation, the x-ray dosage is kept low and as a result, the images tend to have low contrast and include a large amount of noise.

Figure 1:
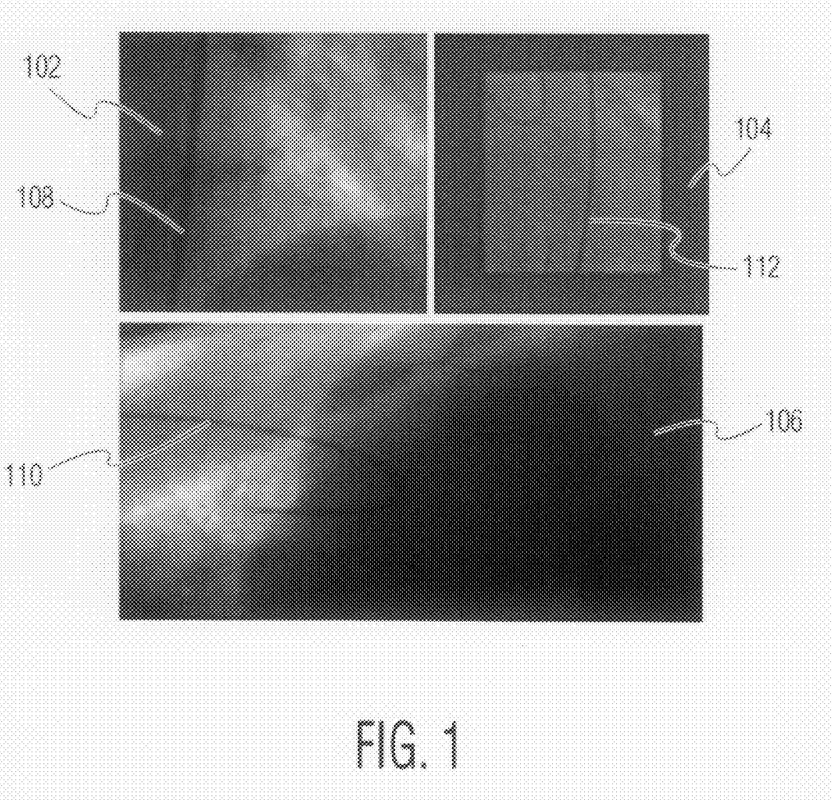
FIG. 1 illustrates a set of example frames of fluoroscopic images that display a catheter, guidewire and wire tip.

As FIG. 1 illustrates, it is often very hard to distinguish the objects of interest, in particular the catheter and guidewire, as shown by images 102-106. The guidewire 108-112 in each image 102-106 is very difficult to detect and could easily be mistaken for part of the anatomy of the patient. Known methods for navigation of the guidewire use a magnet for tracking the guidewire.

Other known methods for guidewire detection use filtering techniques to enhance the guidewire. Some methods report the results as a set of pixels while other methods use splines to model the wire, but only concentrate on the wire tip which has much better visibility than the guidewire. Methods using a set of pixels use a Hessian filter with the purpose of adaptive filtering for image quality enhancement. There is a need for a method for automatically detecting and tracking a guidewire which can enhance the visualization quality of the fluoroscopic data while minimizing the exposure of a patient to x-ray radiation.

SUMMARY OF THE INVENTION

The present invention is directed to a system and method for populating a database with a set of image sequences of an object. The database is used to detect localization of a guidewire in the object. A set of images of anatomical structures is received in which each image is annotated to show a guidewire, catheter, wire tip and stent. For each given image a Probabilistic Boosting Tree (PBT) is used to detect short line segments of constant length in the image. Two segment curves are constructed from the short line segments. A discriminative joint shape and appearance model is used to classify each two segment curve. The shape of an n-segment curve is constructed by concatenating all the two segment curves. A guidewire curve model is identified that comprises a start point, end point and the n-segment curve. The guidewire curve model is stored in the database.

BRIEF DESCRIPTION OF THE DRAWINGS

Preferred embodiments of the present invention will be described below in more detail, wherein like reference numerals indicate like elements, with reference to the accompanying drawings.

DETAILED DESCRIPTION

The present invention is directed to a hierarchical method for learning the shape and appearance of a curve in an image. Such an invention is useful in the detection and segmentation of wire-like structures. An example of this is the detection and segmentation of a guidewire from a fluoroscopy image used during a procedure such as a coronary angioplasty. Such an example will be described in detail however it is to be understood by those skilled in the art that the present invention could be used in other computer vision and medical imagine applications.

In accordance with the present invention, a curve model is learned by closely integrating a hierarchical curve representation using Generative and discriminative models using a hierarchical inference approach. This method will be described in the application of automatic localization of a guidewire in a fluoroscopic image sequence. Typically, in a fluoroscopic image sequence, the guidewire appears as a hardly visible, non-rigid, one-dimensional curve. As will be described in detail hereinafter, the present invention learns the complex shape and appearance of a free-form curve using a hierarchical model of curves of increasing degrees of complexity and a database that includes manual annotations of the guidewire, catheter and stent in the images.

Automatic detection and tracking of the guidewire can greatly aid in enhancing the visualization quality of fluoroscopic data, while minimizing the exposure of the patient to x-ray radiation. In addition, accurate localization of the guidewire can provide useful information for inferring 3D structure in biplane systems, allowing precise navigation of the guidewire tip through the arterial system. The present invention takes into consideration many specific elements that constrain the problem such as noise patterns, shape models, scale, etc. Moreover, by using a large annotated database, a hierarchical representation and a hierarchical computational model, robust results are obtained with great computational efficiency.

Figure 2:
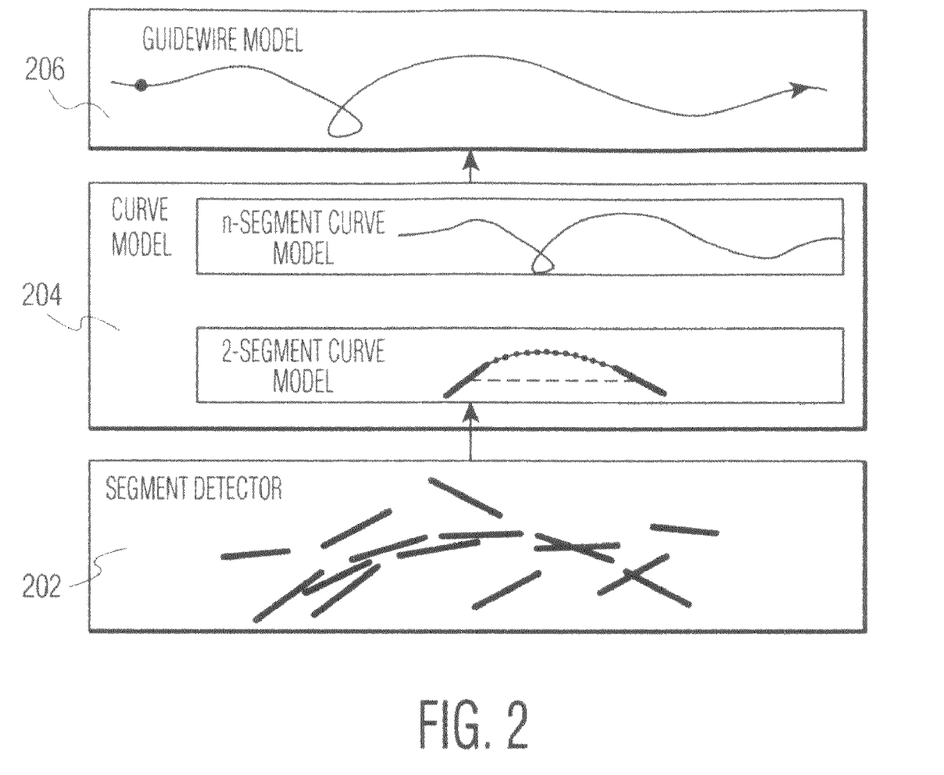
FIG. 2 illustrates a hierarchical model for detecting a curve in accordance with the present invention.

FIG. 2 illustrates a hierarchical model for detecting a curve in accordance with the present invention. The model conceptually comprises three levels. The first level is a segment detector 202, the second level is a curve model 204 and the third level is a guidewire model 206. The hierarchical model uses a learning based strategy that can model the images more accurately and handle the large number of parameters using a coarse-to-fine approach. At all steps, the dimensionality of the search space is the same, but the space granularity varies.

The present invention utilized an approach in which the dimensionality of the search space is gradually increased. As such, suppose that $\Omega$ is the space where a solution of the given problem exists and $P_\Omega$ is the probability that needs to be learned. The learning and computation are performed in a sequence of marginal spaces $$\Omega_1 \subset \Omega_2 \subset \ldots \subset \Omega_n = \Omega \quad (1)$$

such that $\Omega_1$ is a low dimensional space (e.g., 3-dimensional in the guidewire application), and for each k, $\dim(\Omega_k) - \dim(\Omega_{k-1})$ is small. The marginal spaces are chosen in such a way that the marginal probabilities $$P_{\Omega_k}(\theta) = \int_{X \perp \Omega_k} P_\Omega(\theta, x) dx \quad (2)$$

have small entropies, which are reflected in the fact that the learning tasks are easy. A search in the marginal space $\Omega_1$ using the learned probability model finds a subspace $\Pi_1 \subset \Omega_1$ containing the most probable values and discards the rest of the space. The restricted marginal space $\Pi_1$ is then extended to $\Pi_1' = \Pi_1 \times X_1, \subset \Omega_2$. Another stage of learning and detection is performed on $\Pi_1'$ obtaining a restricted marginal space $\Pi_2 \subset \Omega_2$ and the procedure is repeated until the full space $\Omega$ is reached.

At each step, the restricted space $\Pi_k$ is one or two degrees of magnitude smaller than $\Pi_{k-1} \times X_k$, thus obtaining a restricted space n to 2 n degrees of magnitude smaller than $\Omega$. This results in a very efficient algorithm with minimal loss in performance.

In accordance with the present invention, a joint hierarchical model for the curve shape and its appearance are used which closely follows the hierarchy of subspaces as in equation (1). The initial space $\Omega_1$ is the 3-dimensional space of short line segments with position and orientation while for each k>1, $\Omega_k$ models a longer curve than $\Omega_{k-1}$ by extending it with 7 dimensions.

There is a difference between a model for the whole guidewire and a model for a (potentially long) part of a guidewire. This is because a full guidewire model uses the contextual information that the guidewire usually starts from a catheter and ends in a guidewire tip, both structures being very visible. From a marginal space learning perspective, the models for partial guidewires can be regarded as the path to reach the full guidewire model.

Figure 11A:
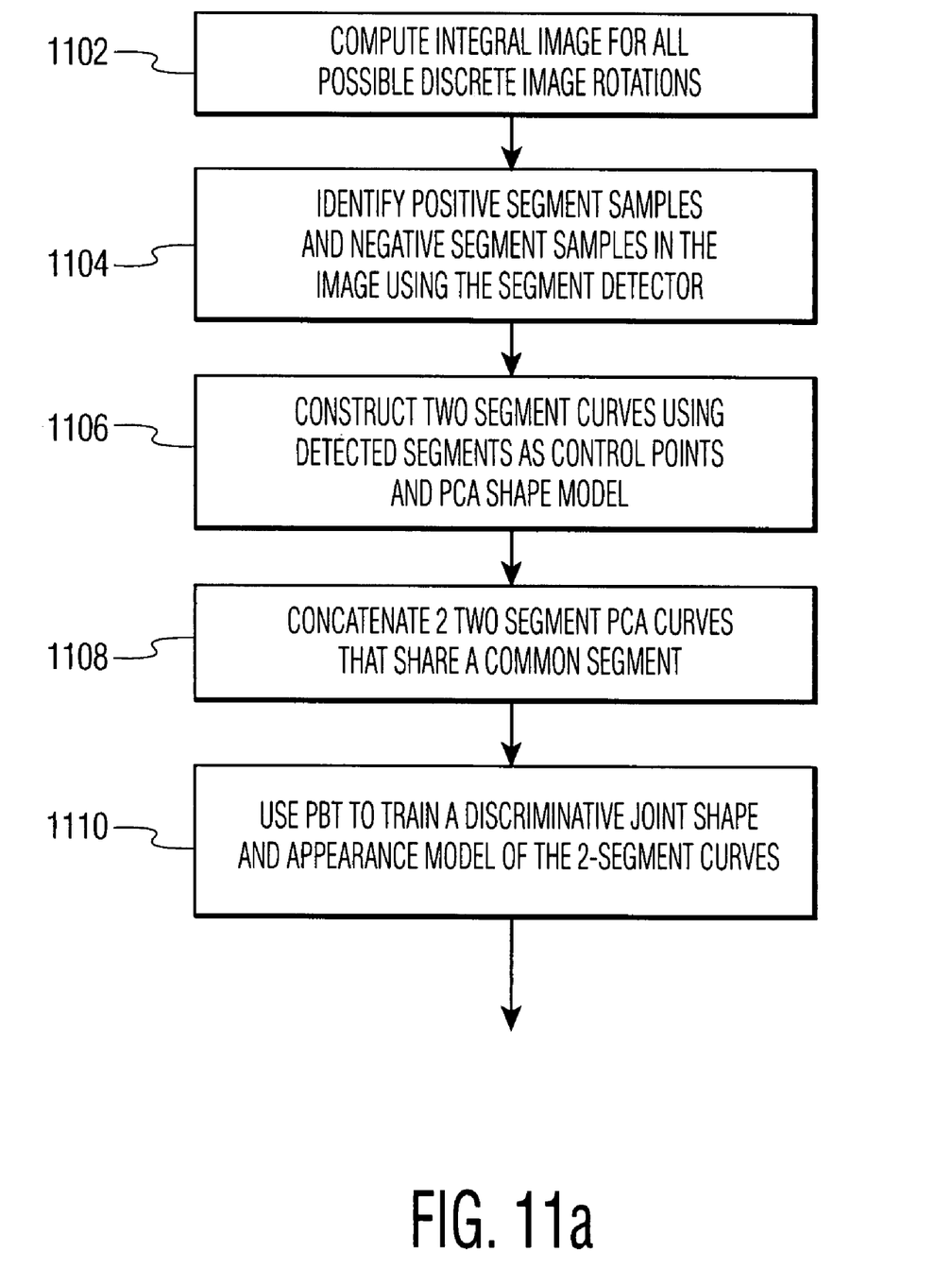
FIGS. 11a and 11b are a flow chart that depicts the steps for detecting a guidewire in an image in accordance with the present invention.
Figure 11B:
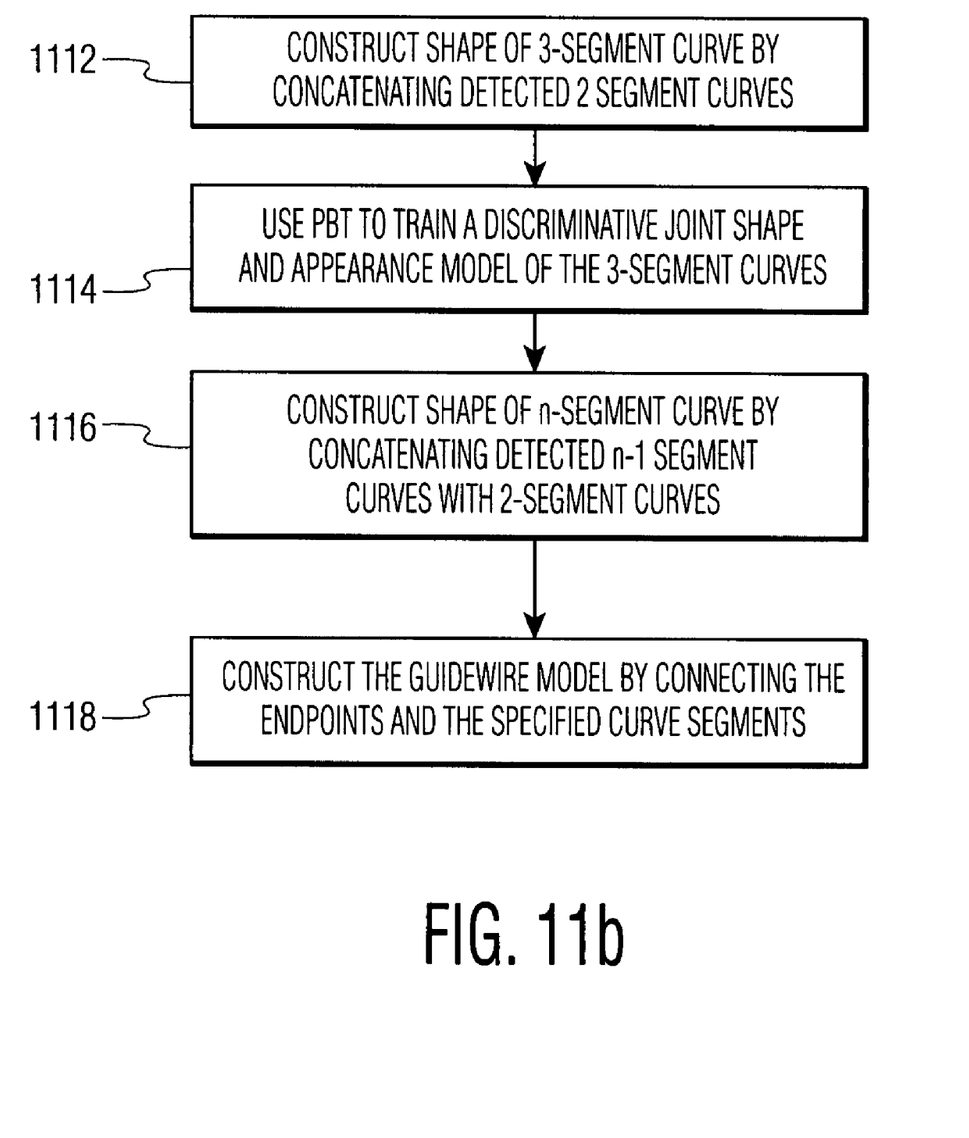

FIG. 11 illustrates a flow chart that depicts the steps for detecting a guidewire in an image in accordance with the present invention. The detectors at all levels of the hierarchical model are trained using a Probabilistic Boosting Tree (PBT). The method is described in detail in co-pending patent application Ser. No. 11/366,722, filed Mar. 2, 2006 and entitled "Probabilistic Boosting Tree Framework for Learning Discriminative Models", which is incorporated by reference in its entirety. The PBT is a method to learn a binary tree from positive and negative samples and to assign a probability to any given sample by integrating the responses from the tree nodes. Each node of the tree is a strong classifier boosted from a number of weak classifiers or features. The PBT is a very powerful and flexible approach that is easy to train and to control against overfitting.

As mentioned above, the first level of the system is a ridge detector aimed at detecting the simplest types of curves, namely short line segments of constant length. These simple curves have three parameters (x, y, $\theta$) where (x, y) is the segment center location and $\theta \in [-90,90]$ is the segment orientation. The space of the orientation is discretized into a plurality of values. For purposes of discussion, 30 values are used.

The segment detector uses a plurality of Haar features and the integral image is computed for all the 30 possible discrete image rotations (step 1102). For example, 22 types of Haar features can be used which are chosen approximately for the task of detecting 1 dimensional structures. The Haar features are restricted to a window centered around the segment sample. The window should be small, e.g., 41×15. There are about 100,000 features for training the segment detector.

Figure 3:
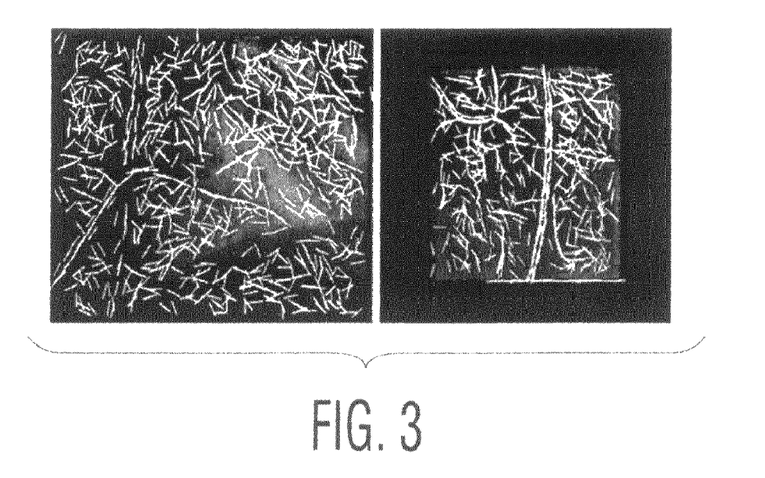
FIG. 3 illustrates the output of the segment detector in accordance with the present invention.

Next, the segment detector is trained to detect segments of length 21 (step 1104). The positive samples for the segment detector are segments of length 21 on the visible guidewire. The negative samples are chosen to be a distance of at least 4 from the annotation. This results in about 166,000 positives and 3.6 million negatives. The detector is a PBT with five levels, of which the first three are enforced as cascade. FIG. 3 shows the output of the segment detector.

Figure 4:
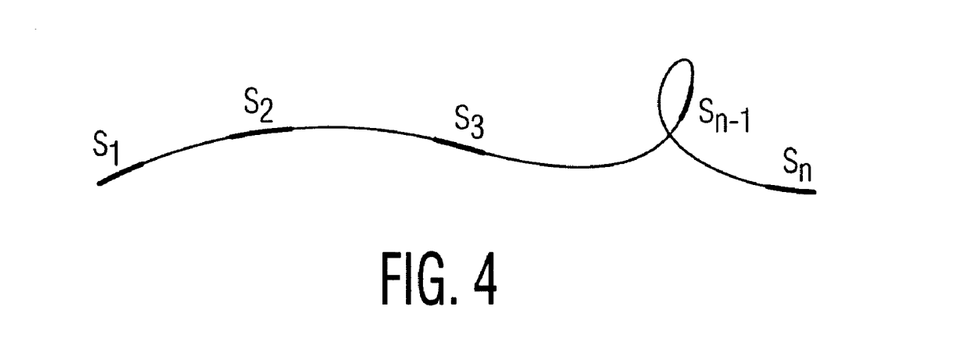
FIG. 4 illustrates how a curve model is controlled by a number of segments identified by the segment detector in accordance with the present invention.

The curve model is designed to handle increasingly longer curves which can ultimately contain the whole guidewire. The curve shape is controlled by a number of segments obtained from the segment detector as shown in FIG. 4. Because the guidewire can have a wide range of lengths, the number of control segments is not fixed and specific models are trained for each number.

To obtain a balance between the degree of generality obtained using descriptive models (e.g., Markov Random Fields) and the capacity to adequately constrain the shape space by generative models (e.g., PCA), the curve shape $C(s_1, \ldots s_n)$ is modeled deterministically from the control segments $s_1, \ldots s_n$ and the obtained curve is verified using a discriminative model based on shape and appearance.

The curve detection approach starts by constructing 2 segment curves using the detected positive segments as control points (step 1106), and a PCA shape model which will be described hereinafter. For each 2 segment curve, its probability is computed. This process of extending the most promising curves and computing their probabilities is repeated for a fixed number of steps. To limit the number of detections at each level, for any given pair of line segments, at most one curve is kept with its starting and ending in that given pair of line segments. This simplification largely limits the number of detections at each level and increases computational efficiency with minimal performance loss.

Figure 5:
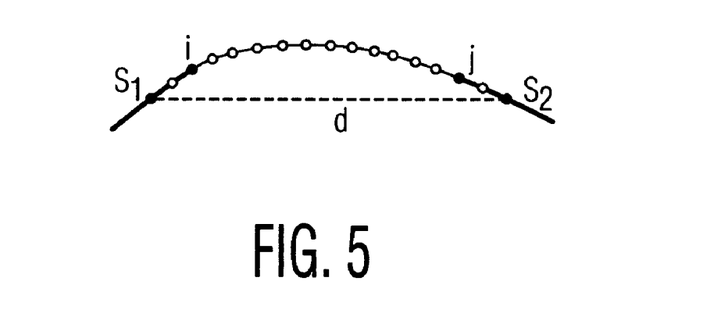
FIG. 5 illustrates how a two segment PCA curve is constructed in accordance with the present invention.

Next PCA curve shape inference is performed. The shape of the 2 segment curves is modeled using a PCA model. These curves are divided into 16 equally distant segments, and thus approximated with 17 equally distant points. To infer the shape of a 2 segment curve, the PCA coefficients are obtained deterministically from the two segments $s_1$, $s_2$ that control the curve as illustrated in FIG. 5. The segments are simultaneously rotated, translated and scaled by the same transformation R so that their centers are at locations (−32, 0) and (32, 0). Then the relative positions $(x_1, y_1)$ and $(x_2, y_2)$ of the segment points at distance 8 from the centers are matched to the intermediate points with index i=3 and j=15, as shown in FIG. 5.

Next, an approach for concatenating two 2 segment PCA curves which share a common segment will be described (step 1108). Let $V^x, V^y, M^x, M^y$ be the x and y-eigenvector matrix (of size 17×4) and the mean shapes. Denoting by A(k) the k-th line of matrix A, the PCA coefficients X of the curve are obtained by solving the linear equation:

$$\begin{pmatrix} V^x(i) \\ V^y(i) \\ V^x(j) \\ V^y(j) \end{pmatrix} X = \begin{pmatrix} x_1 - M^x(i) \\ y_1 - M^y(i) \\ x_2 - M^x(j) \\ y_2 - M^y(j) \end{pmatrix} \quad (3)$$

Figure 6:
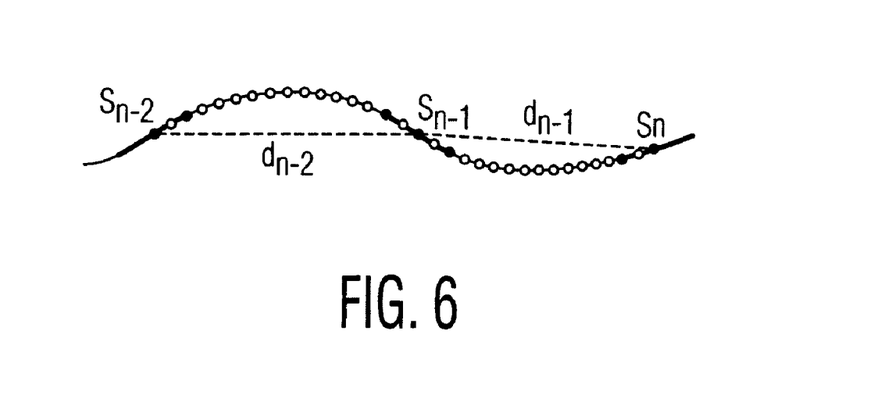
FIG. 6 illustrates how curves are extended by concatenation of the 2 segment PCA curves in accordance with the present invention.

Then all the 17 points of the obtained curve C=M+VX are moved to the true location by the inverse transformation $R^{-1}$, obtaining the curve $C(s_1, s_2)$. The shape of the n-segment curve $C(s_1, \ldots, s_n)$ n≧3 is constructed by concatenating the 2 segment curves $C(s_{k-1}, s_k)$ for all k≦n, as illustrated in FIG. 6.

After the 2 segment PCA curves have been constructed, a discriminative joint shape and appearance model is trained using the PBT (step 1110). To gain computational efficiency, the appearance model is constructed using only information from the segment detector instead of going back to the original data. For the 2 segment curve level, the information from the segment detector comes in the form of a 2 dimensional map of the computed segment probabilities. Based on this map, the features for training the PBT classifier are as follows. Five types of features will be described for training the PBT classifier. However, it is to be understood by those skilled in the art that these features are merely exemplary and that other features can be used to train the PBT classifier without departing from the scope and spirit of the present invention.

The first type of feature is the PCA parameters of the 2 segment curve. The second type of feature is the probability of the best segment at different relative locations both along and perpendicular to the curve. The third type of feature is the dot product of the orientation of the best segment at any of the locations mentioned above and the curve orientation at the projection location. The fourth type of feature is the product of the two corresponding quantities from the second and third features. The fifth type of feature is the size of the largest gaps of the thresholded probability map along the curve, sorted in decreasing order.

Figure 7:
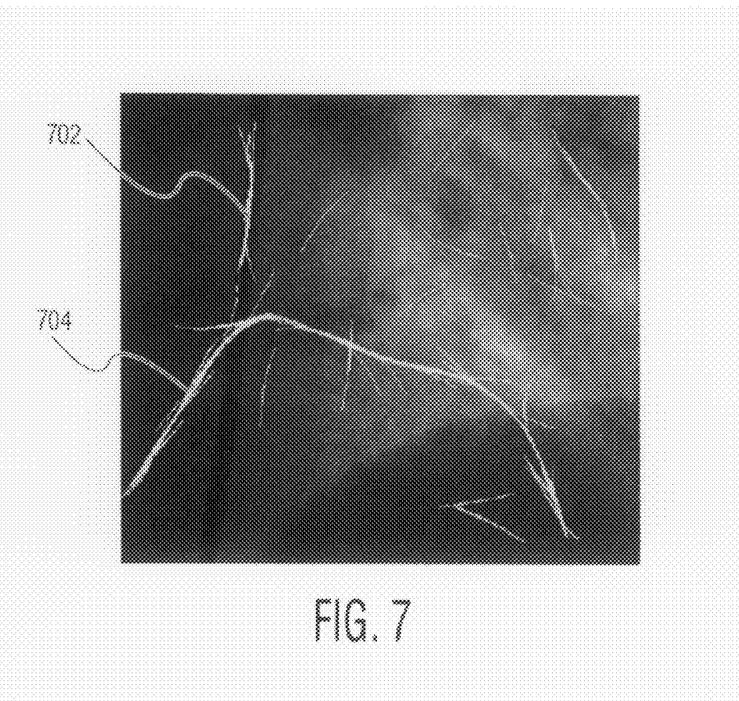
FIG. 7 illustrates an example of the best 1000 2-segment PCA curves in accordance with the present invention.

As can be observed, the feature pool contains features for both shape and appearance and uses the probability map obtained from the low level segment detector as a condensed form of the appearance. Using these features, a PBT can be trained. For example, a PBT with 5 levels can be trained, of which the first two levels are enforced as a cascade. To start, each node has 10 weak classifiers. The positive and negative samples for training are short PCA curves constructed as described above. The positives are the curves with maximum distance two from the annotation, while the negatives have distance at least five from the annotation. This way 26,000 positives and 3 million negatives are obtained. FIG. 7 shows 1000 2-segment curves (e.g., 702 and 704) with the highest probability for image 102 of FIG. 1.

Next the n-segment curve classifier will be described. For each $2<n \leq n_{max}$, a classifier is constructed that is designed to model the shape and appearance of n-segment curves. The shapes of 3-segment curves are constructed by concatenating detected 2 segment curves (step 1112). The classifiers are constructed recursively, the n-segment curve classifier depending on all the k-segment curve classifiers with k<n.

Next, a PUT is used to train a discriminative joint shape and appearance model of the 3-segment curves (step 1114). In accordance with the present invention and for computational efficiency, the n-segment curve classifier is trained using PBT based on the following four types of features. However, it is to be understood by those skilled in the art that these features are merely exemplary and that other features can be used to train the PBT classifier without departing from the scope and spirit of the present invention.

The first type of feature is the features from the 2-segment curve classifier of all the n−1 curve segments from which the curve is composed. The second type of feature is the differences $c_i^j - C_i^k$, i ∈{1, . . . , 4}, j,k,∈1, . . . , n−1 between the corresponding PCA parameters of any two curve segments j, k. The third type of feature is the probabilities of all the 2, 3, . . . , n−1-segment subcurves. The fourth type of feature is the products of probabilities of disjoint subcurves that when concatenated give the whole curve. The shape of the n-segment curve is constructed by concatenating the detected n−1 segment curves with 2-segment curves (step 1116).

Figure 8:
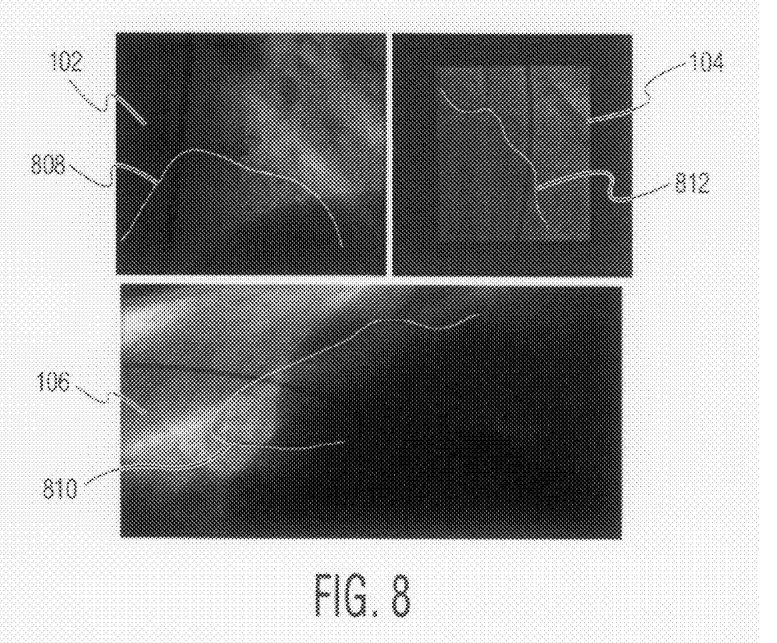
FIG. 8 illustrates the results of the hierarchical curve localization for the images in FIG. 1 in accordance with the present invention.

The positives and negatives at each level are obtained by extending the detection results from the previous level and then keeping as positives samples those sufficiently close to the annotation and as negative samples those sufficiently far from annotation. FIG. 8 shows the images 102, 104, and 106 of FIG. 1, and the curves 808, 810, 812 with the highest probability for each image.

Figure 9:
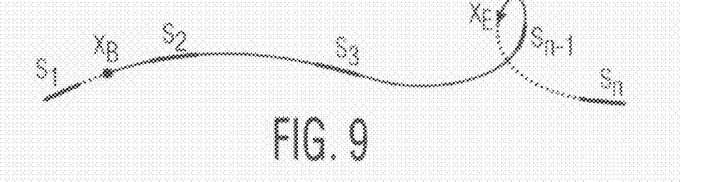
FIG. 9 illustrates a guidewire model that enhances the curve model with a classifier trained to recognize the starting point and the ending point of the guidewire in accordance with the present invention.

The guidewire model extends the curve model with two parameters, the position $x_B$, $x_E$ of the guidewire starting and ending points on the curve segments $C(s_1, s_2)$ and $C(s_{n-1}, s_n)$ as shown in FIG. 9. Thus the guidewire is a curve $G(s_1, \ldots, s_n, x_B, x_E)$, fully specified by the control segments $s_1, \ldots, s_n$ and the endpoints $x_B$, $x_E$ (step 1118). An endpoint detector is trained using the same technique as is used to train the low level segment detector. This way a probability $P_E(x)$ trained to recognize the guidewire endpoints is obtained. The whole guidewire probability is then:

$$P(G(s_1, \ldots, s_n, x_B, x_E)) = P(C(s_1, \ldots, s_n)) P(x_B) P_E(x_E) \quad (4)$$

From each level of the curve hierarchy, the curve with highest probability is augmented to the guidewire model and the parameters $x_B$, $x_E$ are searched on the first and last curve segments. The guidewire with the highest probability is reported as the final localization result.

Figure 10:
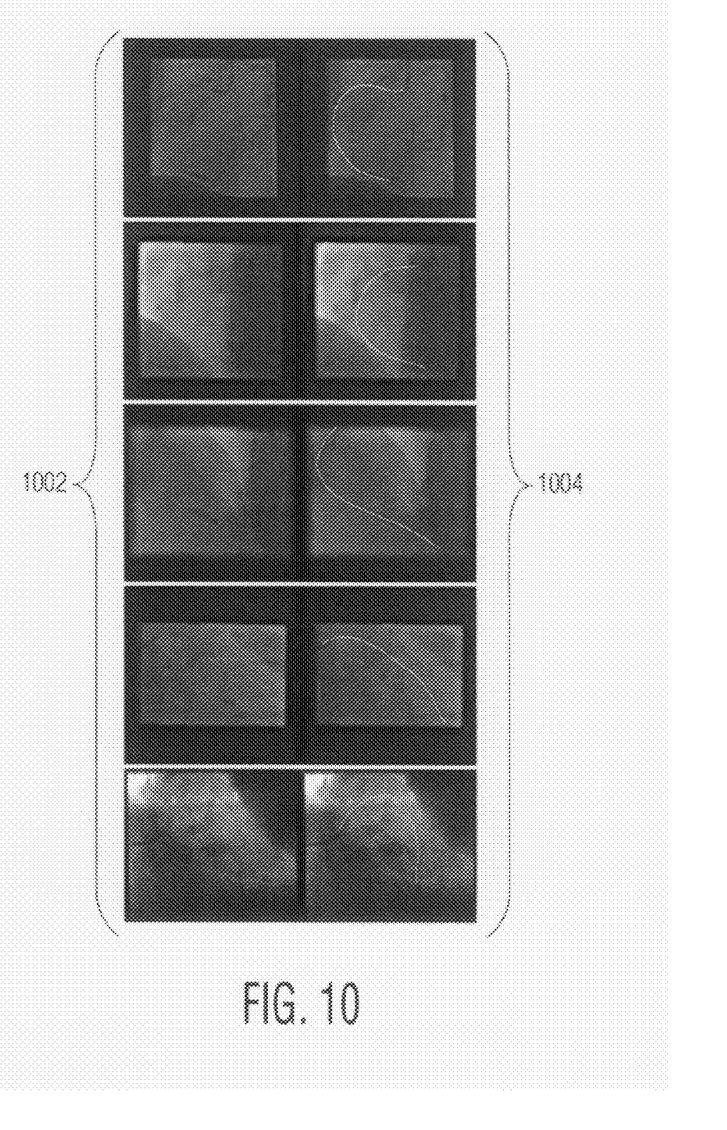
FIG. 10 illustrates a number of images and their counterparts in which a guidewire has been detected in accordance with the present invention.

The present invention presents a hierarchical representational and computational model for the localization of the guidewire in fluoroscopic images. The hierarchical representational model offers advantages in the ability to enforce strong generative and discriminative priors, which together with a learning based approach is capable of obtaining results even where the guidewire is invisible in large areas. The hierarchical computational model based on marginal space learning allows for quick discard of large parts of the search space long before going to the full guidewire model, thereby obtaining great computational speed. FIG. 10 illustrates a series of images and the results obtained using the hierarchical model described herein. Column 1002 represents the original images and column 1004 shows the guidewire curve for each adjacent image in column 1002.

Having described embodiments for a method for detecting curves using hierarchical modeling, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

We claim:

1. A method for populating a database with a set of image sequences of an object the database being used to detect localization of a guidewire in the object, the method comprising the steps of:
    receiving a set of images of anatomical structures, each image being annotated to show a guidewire, catheter, wire tip and stent;
    for each given image:
    using a Probabilistic Boosting Tree (PBT) to detect short line segments of constant length in the image;
    constructing two segment curves from the short line segments;
    using a discriminative joint shape and appearance model to classify each two segment curve;
    constructing a shape of an n-segment curve by concatenating all the two segment curves;
    identifying a guidewire curve model that comprises a start point, end point and the n-segment curve; and
    storing the guidewire curve model in the database.

2. The method of claim 1 wherein the guidewire is represented as a one dimensional curve in a three dimensional space.

3. The method of claim 1 wherein a positive sample comprises a short line segment of constant length.

4. The method of claim 3 wherein the short line segment comprises a segment center location and a segment orientation.

5. The method of claim 4 wherein the segment orientation is discretized into a plurality of discrete image rotation values.

6. The method of claim 5 wherein the image rotation values are represented by Haar features.

7. The method of claim 1 wherein a number of two segment curves detected is controlled by the number of positive samples detected by the segment detector.

8. The method of claim 1 wherein a probability is computed for each two segment curve to determine if the two segment curve is part of the guidewire.

9. The method of claim 1 wherein a Principal Component Analysis model is used to model the shape of each two segment curve.

10. The method of claim 1 wherein the object is an anatomical structure.

11. The method of claim 10 wherein the anatomical structure is a heart.

12. The method of claim 1 wherein the images are fluoroscopic images.

13. A system for detecting localization of a guidewire in an anatomical structure in an image sequence, the system comprising:
    a database that stores a set of image sequences of anatomical structures, each image being annotated to annotated to show a guidewire, catheter, wire tip and stent;
    a processor that receives an input image sequence of an anatomical structure, the processor performing the following steps on each image in the image sequence:
    using a Probabilistic Boosting Tree (PBT) to detect short line segments of constant length in the image;
    constructing two segment curves from the short line segments;
    using a discriminative joint shape and appearance model to classify each two segment curve;
    constructing a shape of an n-segment curve by concatenating all the two segment curves;
    identifying a guidewire curve model that comprises a start point, end point and the n-segment curve;
    constructing the guidewire using the guidewire curve model; and
    a display to display the guidewire in the anatomical structure.

14. The system of claim 13 wherein the guidewire is represented as a one dimensional curve in a three dimensional space.

15. The system of claim 13 wherein a positive sample comprises a short line segment of constant length.

16. The system of claim 15 wherein the short line segment comprises a segment center location and a segment orientation.

17. The system of claim 16 wherein the segment orientation is discretized into a plurality of discrete image rotation values.

18. The system of claim 17 wherein the image rotation values are represented by Haar features.

19. The system of claim 13 wherein a number of two segment curves detected is controlled by the number of positive samples detected by the segment detector.

20. The system of claim 13 wherein a probability is computed for each two segment curve to determine if the two segment curve is part of the guidewire.

21. The system of claim 13 wherein a Principal Component Analysis model is used to model the shape of each two segment curve.

22. The system of claim 13 wherein the anatomical structure is a heart.

23. The system of claim 13 wherein the images are fluoroscopic images.

* * * * *